(12) United States Patent
Helmer

(10) Patent No.: US 12,102,810 B2
(45) Date of Patent: *Oct. 1, 2024

(54) AUDIBLE INDICATOR

(71) Applicant: Sanofi-Aventis Deutschland GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 10 days.

This patent is subject to a terminal disclaimer.

(21) Appl. No.: 17/831,134

(22) Filed: Jun. 2, 2022

(65) Prior Publication Data

US 2022/0288319 A1    Sep. 15, 2022

Related U.S. Application Data

(62) Division of application No. 16/325,599, filed as application No. PCT/EP2017/071194 on Aug. 23, 2017, now Pat. No. 11,369,744.

(30) Foreign Application Priority Data

Aug. 26, 2016   (EP) .................................... 16185802

(51) Int. Cl.
   *A61M 5/31*    (2006.01)
   *A61M 5/20*    (2006.01)
   *A61M 5/315*   (2006.01)

(52) U.S. Cl.
   CPC ........ *A61M 5/3157* (2013.01); *A61M 5/2033* (2013.01); *A61M 2205/43* (2013.01);
   (Continued)

(58) Field of Classification Search
   CPC ............ A61M 5/3157; A61M 2205/43; A61M 2205/58; A61M 2205/581
   See application file for complete search history.

(56) References Cited

U.S. PATENT DOCUMENTS

2,769,643 A    11/1956   Berthold
4,466,426 A *   8/1984   Blackman ........... A61M 5/3158
                                                600/5
(Continued)

FOREIGN PATENT DOCUMENTS

CN    103118723    5/2013
CN    103492001    1/2014
(Continued)

OTHER PUBLICATIONS

International Preliminary Report on Patentability in Application No. PCT/EP2017/071194, dated Feb. 26, 2019, 7 pages.
(Continued)

*Primary Examiner* — Kami A Bosworth
(74) *Attorney, Agent, or Firm* — Fish & Richardson P.C.

(57) ABSTRACT

The present disclosure relates to an audible indicator for use with a drug delivery device, the audible indicator including a spring element configured to reside in one of a relaxed state and a biased state, wherein the audible indicator includes a rotatable element coupled to the spring element, and wherein the spring element releases stored energy to rotate the rotatable element such that the rotatable element impacts a surface to generate an audible signal when the spring element changes from the biased state into the relaxed state.

16 Claims, 4 Drawing Sheets

(52) U.S. Cl.
CPC . *A61M 2205/581* (2013.01); *A61M 2205/582* (2013.01); *A61M 2207/00* (2013.01)

(56) References Cited

U.S. PATENT DOCUMENTS

| | | | |
|---|---|---|---|
| 6,251,098 B1* | 6/2001 | Rake | A61M 5/148 |
| | | | 604/407 |
| 8,850,992 B1 | 10/2014 | Akpaffiong | |
| 2004/0054326 A1* | 3/2004 | Hommann | F16F 1/10 |
| | | | 604/131 |
| 2006/0106342 A1* | 5/2006 | Cox | A61M 5/3287 |
| | | | 604/110 |
| 2013/0317432 A1 | 11/2013 | Fabien et al. | |
| 2013/0317435 A1 | 11/2013 | Fabien et al. | |
| 2013/0317479 A1 | 11/2013 | Brereton et al. | |
| 2016/0121050 A1 | 5/2016 | Fabien | |
| 2016/0184521 A1 | 6/2016 | Edwards et al. | |
| 2017/0014574 A1* | 1/2017 | Ogawa | A61M 5/3137 |
| 2017/0232201 A1 | 8/2017 | Holland et al. | |
| 2018/0185581 A1 | 7/2018 | Fabien | |

FOREIGN PATENT DOCUMENTS

| | | |
|---|---|---|
| CN | 103492002 | 1/2014 |
| CN | 104394909 | 3/2015 |
| CN | 105283209 | 1/2016 |
| CN | 105579083 | 5/2016 |
| CN | 105722538 | 6/2016 |
| CN | 106573114 A | 4/2017 |
| EP | 2489385 | 8/2012 |
| JP | 2014-508000 | 4/2014 |
| JP | 2015-510424 | 4/2015 |
| WO | WO 2012/022810 | 2/2012 |
| WO | WO 2012/110578 | 8/2012 |
| WO | WO 2012/110583 | 8/2012 |
| WO | WO 2013/124139 | 8/2013 |
| WO | WO 2014/191190 | 12/2014 |
| WO | WO 2015/004048 | 1/2015 |
| WO | WO 2015/052224 | 4/2015 |
| WO | WO 2015/151693 | 10/2015 |
| WO | WO 2016/001592 | 1/2016 |
| WO | WO 2016/027096 | 2/2016 |
| WO | WO 2016/114985 | 7/2016 |
| WO | WO 2016/120587 | 8/2016 |

OTHER PUBLICATIONS

International Search Report and Written Opinion in Application No. PCT/EP2017/071194, dated Oct. 10, 2017, 10 pages.

* cited by examiner

AUDIBLE INDICATOR

CROSS REFERENCE TO RELATED APPLICATIONS

The present application is a divisional application of the U.S. patent application Ser. No. 16/325,599, filed Feb. 14, 2019, which is the national stage entry of International Patent Application No. PCT/EP2017/071194, filed on Aug. 23, 2017, and claims priority to Application No. EP 16185802.2, filed on Aug. 26, 2016, the disclosures of which are incorporated herein by reference.

TECHNICAL FIELD

The present disclosure relates to an audible indicator for use with a drug delivery device.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Furthermore, the force required to push the button/plunger may be too high (e.g., if the user is elderly or a child). And, aligning the injection device, administering the injection, and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Furthermore, it is desirable to administer the full dose in order to achieve full effectiveness of the medicament within the patient.

Thus, there remains a need for an audible indicator for a drug delivery device. Current indicators may be too quiet or too bulky to use in current autoinjectors and other drug delivery devices. The audible indicator described herein solves one or more of these problems.

SUMMARY

An object of the present disclosure is to provide an improved audible indicator for use with a drug delivery device.

The object is achieved by an audible indicator according to claim 1.

Exemplary embodiments are provided in the dependent claims.

According to the present disclosure, an audible indicator for use with a drug delivery device includes a spring element configured to reside in one of a relaxed state and a biased state, wherein the audible indicator further includes a rotatable element coupled to the spring element and rotatable about a pivot, wherein the spring element releases stored energy to rotate the rotatable element such that the rotatable element impacts a surface to generate an audible signal when the spring element changes from the biased state into the relaxed state.

In the context of the present application, the relaxed state is a state in which the spring element has a relatively low potential energy whereas the biased state is a state in which the spring element has a potential energy which is higher than in the relaxed state. When the spring element changes from the biased state into the relaxed state, stored energy is released from the spring element.

The audible indicator can be used for indicating to a patient or user that the full dose of medicament in the drug delivery device was spent. Thus, the drug delivery device is improved in order to achieve a reliable indication of the end of medicament delivery and a full effectiveness of the medicament within the patient.

In an exemplary embodiment, the spring element is engaged in a slot within the rotatable element thus coupling the spring element to the rotatable element for joint rotation. The rotatable element can thus be rotated by the spring element changing from the biased state to the relaxed state and the spring element can be moved from the relaxed state into the biased state by rotating the rotatable element.

In an exemplary embodiment, the rotatable element includes a first leg and a second leg substantially arranged in an L-shape. This allows for a space saving arrangement of the audible indicator in the drug delivery device.

In an exemplary embodiment, the rotatable element includes a pivot bore configured to be rotatably mounted on a bearing pin. The bearing pin may be fixed in the drug delivery device, e.g. on a case thereof. Alternatively, the rotatable element may include a pivot axle configured to be mounted in a bore, which may be arranged in the drug delivery device, e.g. in a case thereof.

In an exemplary embodiment, the first leg includes a curved section near the pivot bore towards a free end. While the first leg may have a substantially straight section between the intersection of the first and second legs and the pivot bore for abutting against the case of the drug delivery device in the pre-release state, the curved section may be provided on the first leg near the pivot bore towards the free end of the first leg allowing for rotation of the rotatable element until an end face of the free end abuts the front case in a released state so that the rotatable element has two well defined positions within the drug delivery device.

In an exemplary embodiment, the pivot bore includes a V-slot allowing the pivot bore to be laterally clicked onto the bearing pin, i.e. the V-slot may extend from an axis of the pivot bore in a radial direction and, in order to click the pivot bore onto the bearing pin, the pivot bore and the bearing pin are aligned with their axes substantially parallel, the V-slot facing the bearing pin and the pivot bore is moved towards the bearing pin until the axes of the pivot bore and the bearing pin substantially fall in line. This facilitates assembly of the audible indicator into the drug delivery device.

In an exemplary embodiment, the spring element includes a beam and a flag part protruding from one end of the beam substantially at right angles, wherein the flag part is adapted to engage in the slot. In an exemplary embodiment, the spring element has a substantially straight shape in the relaxed state and is configured to be resiliently flexed out of this straight shape into a curved shape in the biased state.

In an exemplary embodiment, a free end of the second leg is adapted to radially inwardly abut the plunger in order to maintain the audible indicator in a pre-release state.

In an exemplary embodiment, the rotatable element and/or the spring element are metal parts, in particular sheet metal parts, which may be manufactured in a one stamp-bend production process. This allows for a particularly cost efficient production of the audible indicator.

In an exemplary embodiment, a drug delivery device includes a case, a plunger and an audible indicator including a spring element configured to reside in one of a relaxed state and a biased state, wherein the audible indicator includes a rotatable element coupled to the spring element and rotatable about a pivot, wherein the spring element releases stored energy to rotate the rotatable element such that the rotatable element impacts a surface of the case to generate an audible signal when the spring element changes from the biased state into the relaxed state. This may also provide a tactile feedback for the user of the drug delivery device holding the drug delivery device with his hand.

The case may be adapted to hold a medicament container, such as a syringe.

The resilient force member may change from the biased state into the relaxed state by a movement of a plunger that is used to displace the drug from a medicament container. For example, the resilient force member may change from the biased state into the relaxed state when the plunger moves towards or reaches a distal position at the end of a medicament delivery process.

In an exemplary embodiment, the rotatable element includes a pivot bore configured to be rotatably mounted on a bearing pin. The bearing pin may be fixed in the drug delivery device, e.g. on a case thereof. Alternatively, the rotatable element may include a pivot axle configured to be mounted in a bore, which may be arranged in the drug delivery device, e.g. in a case thereof.

The case may include a front case and a rear case and the bearing pin may be arranged on one of the front case and the rear case while the rotatable element may impact the other one of the front case and the rear case. In other embodiments, the rotatable element may impact the one of the front case and the rear case on which the bearing pin is arranged. In yet another embodiment, the case may be one-part.

In an exemplary embodiment, the pivot bore includes a V-slot allowing the pivot bore to be laterally clicked onto the bearing pin, i.e. the V-slot may extend from an axis of the pivot bore in a radial direction and, in order to click the pivot bore onto the bearing pin, the pivot bore and the bearing pin are aligned with their axes substantially parallel, the V-slot facing the bearing pin and the pivot bore is moved towards the bearing pin until the axes of the pivot bore and the bearing pin substantially fall in line. This facilitates assembly of the audible indicator into the drug delivery device.

In an exemplary embodiment, the rotatable element includes a first leg and a second leg substantially arranged in an L-shape, wherein a free end of the second leg is adapted to radially inwardly abut the plunger in order to maintain the audible indicator in a pre-release state.

In an exemplary embodiment, an aperture is provided in the case for holding the beam.

A method of producing an audible indicator for use with a drug delivery device may include:

forming a spring element configured to reside in one of a relaxed state and a biased state, forming a rotatable element adapted to be coupled to the spring element and rotatable about a pivot, wherein the spring element and the rotatable element are manufactured in a one stamp-bend production process on a stamp-bend automat. This allows for a particularly cost efficient production of the audible indicator.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

In the present application, when the term "distal section/end" is used, this refers to the section/end of the device, or the sections/ends of the components thereof, which during use of the device is located closest to a medicament delivery site of a patient. Correspondingly, when the term "proximal section/end" is used, this refers to the section/end of the device, or the sections/ends of the components thereof, which during use of the device is pointing away from the medicament delivery site of the patient.

Figure 1:
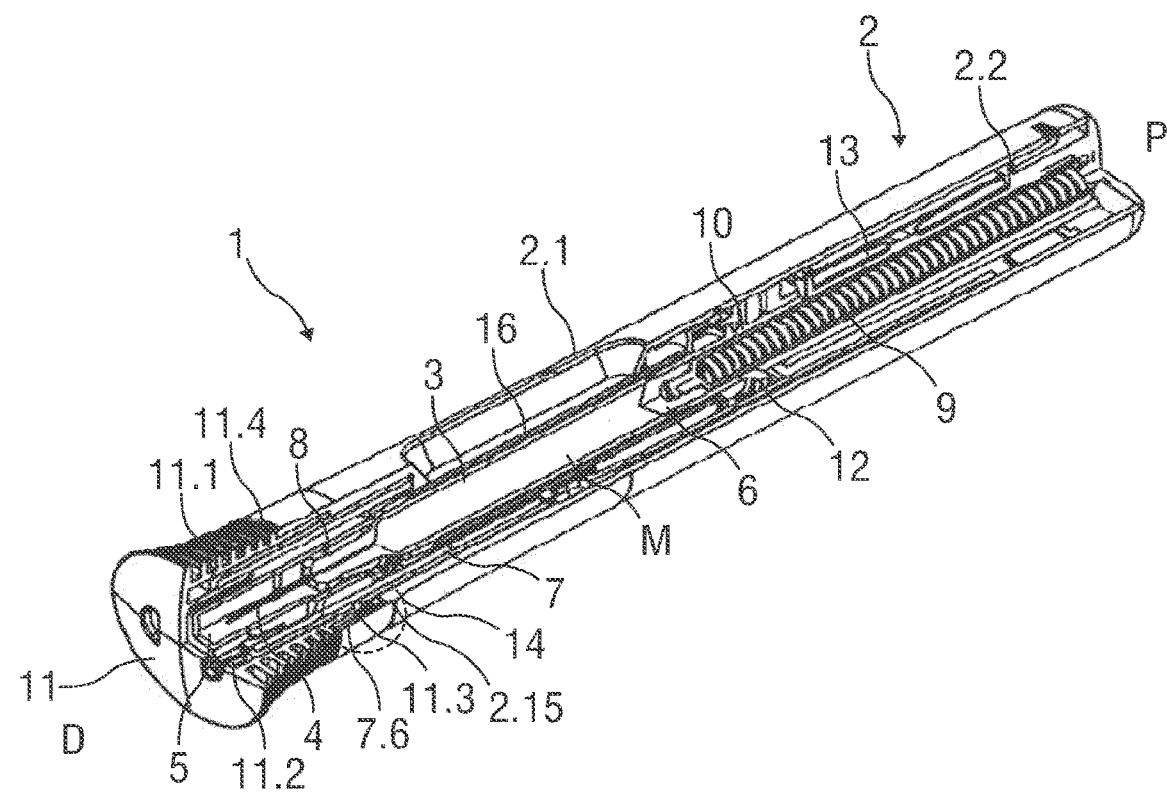
FIG. 1 is a schematic perspective partial section of a drug delivery device including an audible indicator.

FIG. 1 shows an exemplary embodiment of a drug delivery device 1, which may be configured as an autoinjector.

In the exemplary embodiment, the drug delivery device 1 includes a case 2 with a front case 2.1 and a rear case 2.2. The case 2 is adapted to hold a medicament container 3, such as a syringe. (The medicament container is referred to hereinafter as the "syringe 3"). The syringe 3 may be a pre-filled syringe, in particular a 1.0 ml pre-filled syringe, containing a medicament M and having a needle 4 arranged at a distal end of the syringe 3. In another exemplary embodiment, the medicament container 3 may be a cartridge which includes the medicament M and engages a removable needle (e.g. by threads, snaps, friction, etc.).

The drug delivery device 1 further includes a protective needle sheath 5 that is coupled to the needle 4. For example, the protective needle sheath 5 is removably coupled to the needle 4. The protective needle sheath 5 may be a rubber needle sheath or a rigid needle sheath which is composed of rubber and a full or partial plastic shell.

For sealing the syringe 3 proximally and for displacing a medicament M contained in the syringe 3 through the needle 4, a stopper 6 is provided and arranged within the syringe 3.

In the illustrated embodiment, the drug delivery device 1 includes a needle shroud 7 that is telescopically coupled to the case 2 and movable between a first extended position relative to the case 2 in which the needle 4 is covered and a retracted position relative to the case 2 in which the needle 4 is exposed. Furthermore, a shroud spring 8 is arranged to bias the needle shroud 7 distally against the case 2.

Furthermore, a drive spring 9 is arranged within the case 2. A plunger 10 serves for forwarding a force of the drive spring 9 to the stopper 6. The plunger 10 may be hollow, wherein the drive spring 9 is arranged within the plunger 10 biasing the plunger 10 distally against the case 2. In another exemplary embodiment, the plunger 10 may be solid and the drive 9 may engage a proximal end of the plunger 10. In the illustrated embodiment, the drive spring 9 is wrapped around an outer diameter of the plunger 10 and extends within the syringe 3.

Additionally, the drug delivery device 1 includes a cap 11 that may be removably disposed at a distal end of the case 2, in particular at a distal end of the front case 2.1. The cap 11 may include grip features 11.1 for facilitating a removal of the cap 11, e.g., by twisting and/or pulling the cap 11 off the case 2. The cap 11 may further include a grip element 11.2, e.g. a barb, a hook, a narrowed section, etc., arranged to engage the protective needle sheath 5, the case 2 and/or the needle shroud 7.

In the illustrated embodiment, a plunger release mechanism 12 is arranged for preventing release of the plunger 10 prior to retraction of the needle shroud 7 relative to the case 2 and for releasing the plunger 10 once the needle shroud 7 is sufficiently retracted.

Furthermore, a shroud lock mechanism 14 is arranged to prevent retraction of the needle shroud 7 relative to the case 2 when the cap 11 is in place, thereby avoiding unintentional activation of the drug delivery device 1, e.g., if dropped, during shipping or packaging, etc. The shroud lock mechanism 14 may include one or more compliant beams 11.3 on the cap 11 and a respective number of apertures 7.6 in the needle shroud 7 adapted to receive each of the compliant beams 11.3.

When the cap 11 is attached to the drug delivery device 1, the compliant beams 11.3 abut a radial stop 2.15 on the case 2 which prevents the compliant beams 11.3 from disengaging the apertures 7.6. Furthermore, when the cap 11 is attached to the drug delivery device 1, an axial proximal movement of the cap 11 relative to the case 2 is limited by a rib 11.4 on the cap 11 that abuts the case 2.

When the cap 11 is pulled off the case 2 distally, the compliant beams 11.3 may abut an edge of the aperture 7.6 and deflect to disengage the aperture 7.6, allowing for removal of the cap 11 and the protective needle sheath 5 attached thereto. In an exemplary embodiment, the compliant beams 11.3 and/or the apertures 7.6 may be ramped to reduce force necessary to disengage the compliant beams 11.3 from the apertures 7.6.

The drug delivery device 1 further includes an audible indicator 13 for producing an audible feedback for a user or patient indicating completion of medicament delivery. In other words: The audible indicator 13 is provided to indicate to a user or a patient that the full dose of medicament M was spent.

The drug delivery device 1 further may include a carrier 16 to allow an accurate support of the syringe 3 during and after an assembling process. The carrier 16 is adapted to mount, position and hold the syringe 3 within the case 2.

In the following FIGS. 2 to 5, the audible indicator 13 will be explained in more detail.

Figure 2:
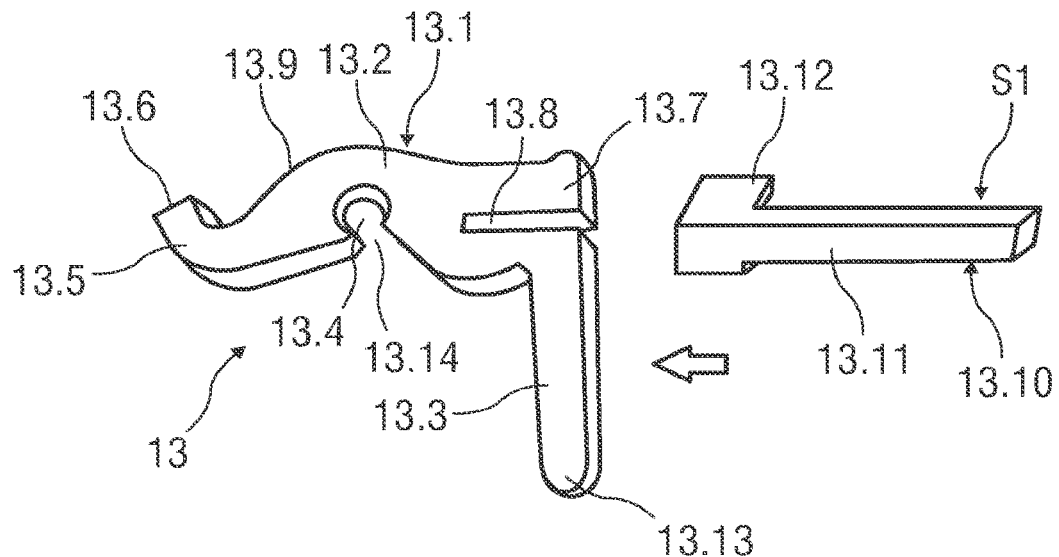
FIG. 2 is a schematic exploded view of the audible indicator.
Figure 3:
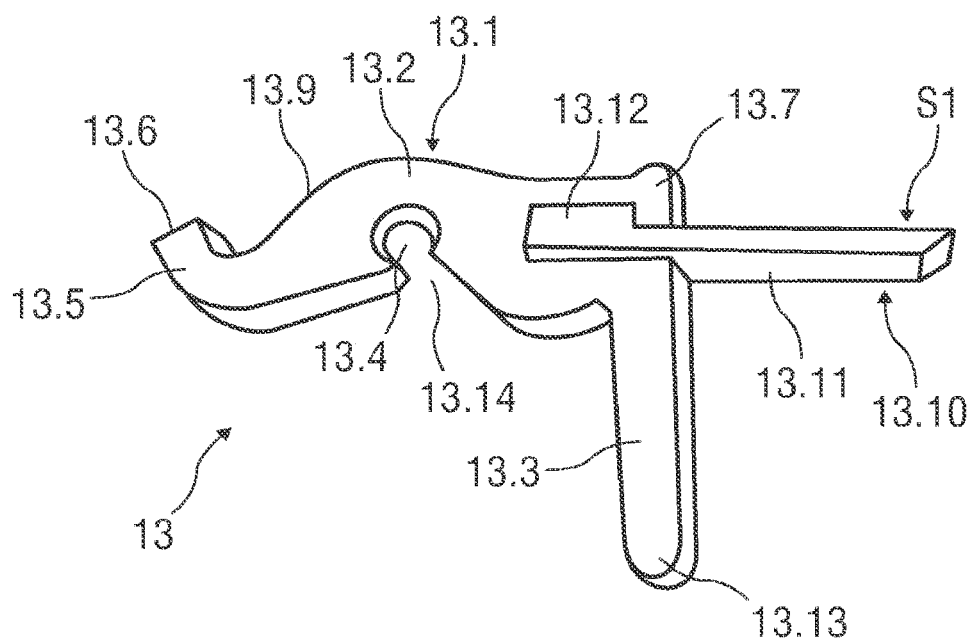
FIG. 3 is a schematic view of the audible indicator.
Figure 4:
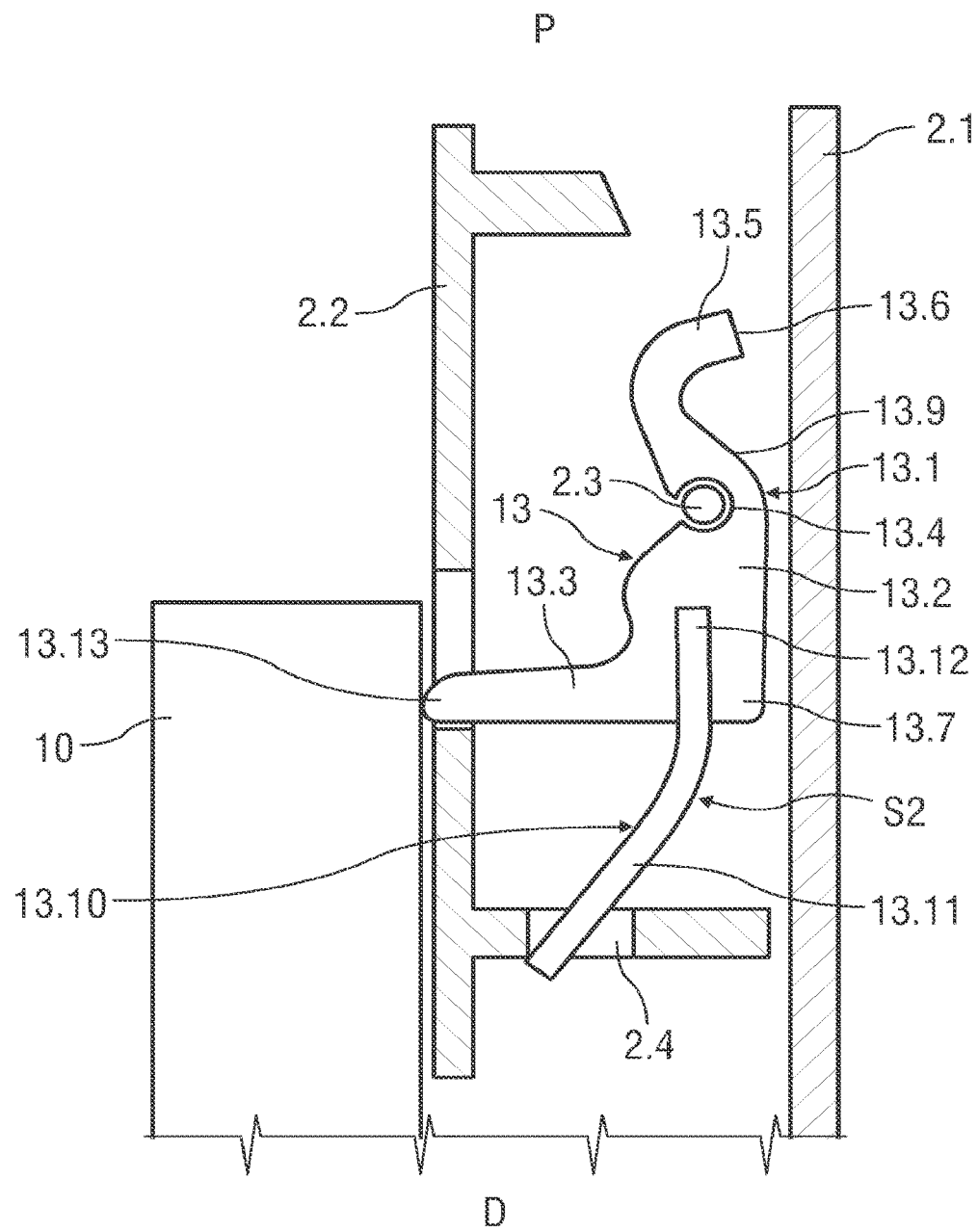
FIG. 4 is a schematic view of the audible indicator located in the drug delivery device in a pre-release state.
Figure 5:
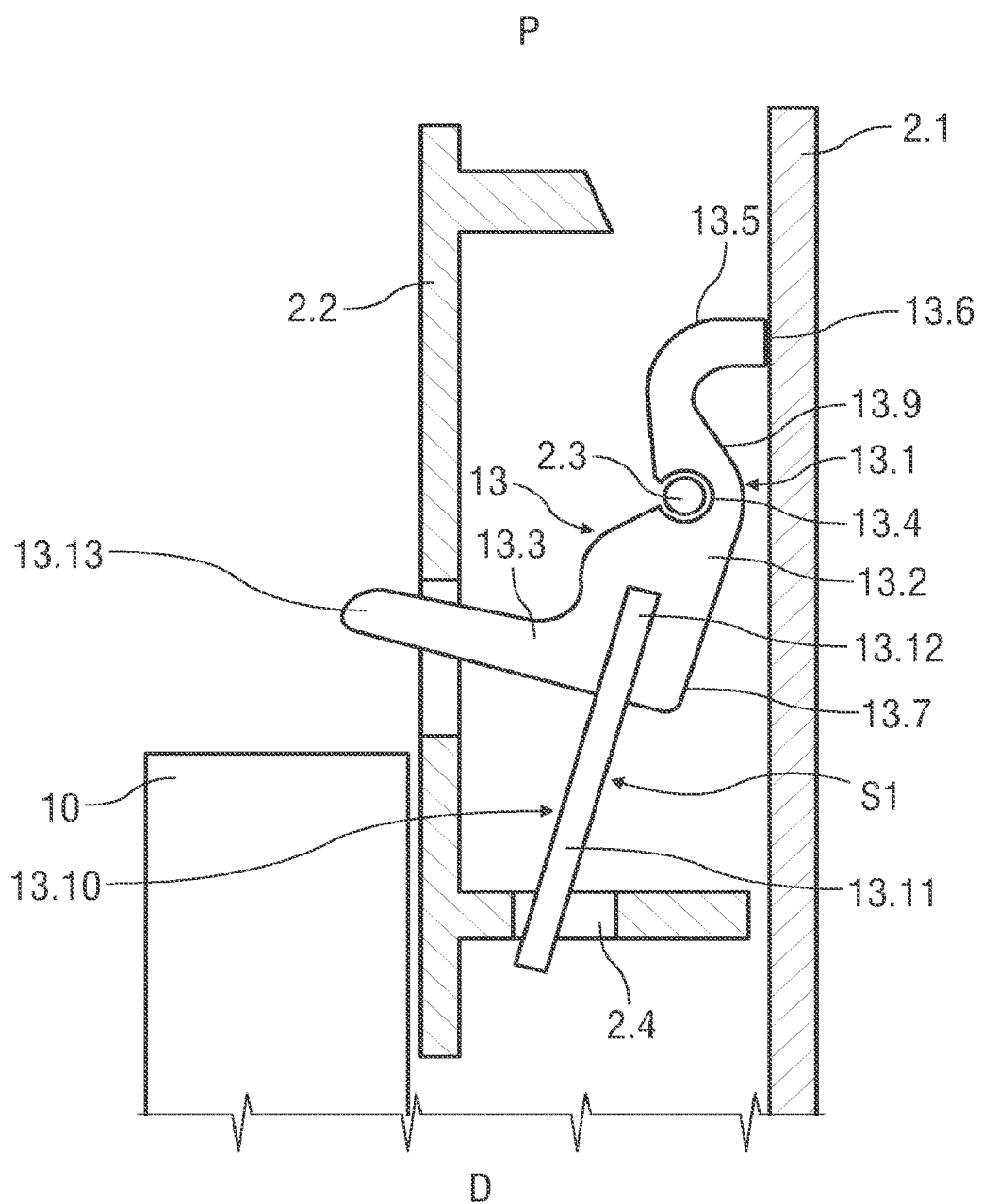
FIG. 5 is a schematic view of the audible indicator located in the drug delivery device in a released state.

FIGS. 2 and 3 are schematic views of the audible indicator 13, wherein FIG. 2 shows the audible indicator 13 in an exploded view FIG. 3 in a partly assembled state. FIG. 4 shows the audible indicator 13 located in the drug delivery device 1 in a pre-release state and FIG. 5 shows the audible indicator 13 located in the drug delivery device 1 in a released state.

The audible indicator 13 includes a rotatable element 13.1 which may consist of sheet metal. The rotatable element 13.1 may include a first leg 13.2 and a second leg 13.3 substantially arranged in an L-shape. The first leg 13.2 may include a pivot bore 13.4 arranged to be rotatably mounted on a bearing pin 2.3 which may be provided in the rear case 2.2 such that the second leg 13.3 is directed substantially radially inwards. A free end 13.5 of the first leg 13.2 may be angled and have an end face 13.6 directed substantially radially outwards when the rotatable element 13.1 is located on the bearing pin 2.3. An end opposite the free end 13.5 of the first leg 13.2 is connected to the second leg 13.3 thereby forming an intersection 13.7 and includes a slot 13.8. While the first leg 13.2 may have a substantially straight section between the intersection 13.7 and the pivot bore 13.4 for abutting against the front case 2.1 in the pre-release state, a curved section 13.9 may be provided on the first leg 13.2 near the pivot bore 13.4 towards the free end 13.5 allowing for rotation of the rotatable element 13.1 until the end face 13.6 abuts the front case 2.1 in a released state.

Alternatively, instead of the pivot bore 13.4, the rotatable element 13.1 may include any kind of pivot, e.g. a pivot axle configured to be mounted in a bore, which may be arranged in the drug delivery device 1, e.g. in the case 2 thereof.

The audible indicator 13 furthermore includes a spring element 13.10 including a beam 13.11 and a flag part 13.12 protruding from one end of the beam 13.11 substantially at right angles. The flag part 13.12 is adapted to engage in the slot 13.8 in the rotatable element 13.1 such that the rotatable element 13.1 may be rotated by the spring element 13.10. The beam 13.11 is adapted to be held in an aperture 2.4 in the rear case 2.2. The spring element 13.10 may have a substantially straight shape in a relaxed state S1 and may be resiliently flexed out of this straight shape into a curved shape in a biased state S2.

A free end 13.13 of the second leg 13.3 is adapted to radially inwardly abut the plunger 10 prior to the plunger 10 being released in order to maintain the audible indicator in the pre-release state, in which the spring element 13.10 is in the biased state S2 (cf. FIG. 4) and biases the second leg 13.3 inwards towards the plunger 10. The end face 13.6 is radially spaced from the front case 2.1.

For delivering the medicament M through the needle 4 into an injection site, e.g. a patient's skin, the plunger 10 is moved distally from a drive spring 9 to a distal position due to an activation of the drive spring 9. The activation of the drive spring 9 may be initiated by pressing a button or by depressing the needle shroud 7 as it is pushed against the injection site thus causing the plunger release mechanism 12 to release the plunger 10.

As the plunger 10 is released, the plunger 10 is advanced in the distal direction D driven by the drive spring 9. At the end of dose or immediately prior to this the plunger 10 has travelled so far in the distal direction D that it no longer engages the second leg 13.3 which can hence move further inwards under the bias from the spring element 13.10 so that the rotatable element 13.1 rotates and the end face 13.6 impacts the front case 2.1 generating an audible feedback. A loudness of the audible feedback depends on a pre-load of the spring element 13.10 in its biased state S2. The spring element 13.10 relaxes and returns to its relaxed state 51. The user or patient recognizing the audible signal knows that the medicament delivery process is finished and that the full dose was delivered.

The rotatable element 13.1 and the spring element 13.10 may be metal parts, in particular sheet metal parts, which may be manufactured in a one stamp-bend production process.

The pivot bore 13.4 may be partially open including a V-slot 13.14 allowing the pivot bore 13.4 to be laterally clicked onto the bearing pin 2.3.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, ora sulphated polysaccharide, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations including (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
1.1 drive sub assembly
2 case
2.1 front case
2.2 rear case
2.3 bearing pin
2.4 aperture
2.15 radial stop
3 medicament container, syringe
4 needle
5 protective needle sheath
6 stopper
7 needle shroud
7.6 apertures
8 shroud spring
9 drive spring
10 plunger
11 cap
11.1 grip features
11.2 grip element
11.3 compliant beams
11.4 rib
12 plunger release mechanism
13 audible indicator
13.1 rotatable element
13.2 first leg
13.3 second leg
13.4 pivot bore
13.5 free end
13.6 end face
13.7 intersection
13.8 slot
13.9 curved section
13.10 spring element
13.11 beam
13.12 flag part
13.13 free end 13.14 V-slot
14 shroud lock mechanism
D distal direction
P proximal direction
S1 relaxed state
S2 biased state

The invention claimed is:

1. An audible indicator for use with a drug delivery device, the audible indicator comprising:
   a spring element configured to reside in one of a relaxed state and a biased state; and
   a rotatable element coupled to the spring element and rotatable about a pivot,
   wherein the rotatable element is configured to impact a surface,
   wherein the spring element and the rotatable element are arranged such that, when the spring element releases stored energy, the rotatable element rotates and is configured to impact the surface to generate an audible signal when the spring element changes from the biased state into the relaxed state,
   wherein the spring element is engaged in a slot within the rotatable element, and
   wherein the spring element is a sheet metal part.

2. The audible indicator according to claim 1, wherein the rotatable element comprises a first leg and a second leg substantially arranged in an L-shape.

3. The audible indicator according to claim 2, wherein the rotatable element comprises a pivot bore.

4. The audible indicator according to claim 3, wherein the first leg comprises a curved section near the pivot bore towards a free end.

5. The audible indicator according to claim 3, wherein the pivot bore comprises a V-slot.

6. The audible indicator according to claim 1, wherein the spring element has a substantially straight shape in the relaxed state and is configured to be resiliently flexed out of the straight shape into a curved shape in the biased state.

7. The audible indicator according to claim 1, wherein the rotatable element is a sheet metal part.

8. The audible indicator according to claim 1, wherein the spring element and the rotatable element are manufactured in a one stamp-bend production process on a stamp-bend automat.

9. An audible indicator for use with a drug delivery device according to claim 1, the audible indicator comprising:
   a spring element configured to reside in one of a relaxed state and a biased state; and
   a rotatable element coupled to the spring element and rotatable about a pivot,
   wherein the rotatable element is configured to impact a surface,
   wherein the spring element and the rotatable element are arranged such that, when the spring element releases stored energy, the rotatable element rotates and is configured to impact the surface to generate an audible signal when the spring element changes from the biased state into the relaxed state,
   wherein the spring element is engaged in a slot within the rotatable element, and
   wherein the spring element comprises a beam and a flag part protruding from one end of the beam substantially at a right angle, wherein the flag part is adapted to engage in the slot.

10. The audible indicator according to claim 9, wherein the rotatable element comprises a first leg and a second leg substantially arranged in an L-shape.

11. The audible indicator according to claim 10, wherein the rotatable element comprises a pivot bore.

12. The audible indicator according to claim 11, wherein the first leg comprises a curved section near the pivot bore towards a free end.

13. The audible indicator according to claim 11, wherein the pivot bore comprises a V-slot.

14. The audible indicator according to claim 9, wherein the spring element has a substantially straight shape in the relaxed state and is configured to be resiliently flexed out of the straight shape into a curved shape in the biased state.

15. The audible indicator according to claim 9, wherein the rotatable element is a sheet metal part.

16. The audible indicator according to claim 9, wherein the spring element and the rotatable element are manufactured in a one stamp-bend production process on a stamp-bend automat.

* * * * *